United States Patent
Dubey et al.

(10) Patent No.: US 10,250,979 B2
(45) Date of Patent: Apr. 2, 2019

(54) ELECTROMAGNETIC ACOUSTIC TRANSDUCER EXCITATION SOURCE WITH PROGRAMMABLE TONE BURST GENERATOR

(71) Applicant: Council of Scientific & Industrial Research, New Delhi (IN)

(72) Inventors: P K Dubey, New Delhi (IN); V N Ojha, New Delhi (IN); Shashank Singh, New Delhi (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 15/828,801

(22) Filed: Dec. 1, 2017

(65) Prior Publication Data

US 2018/0160229 A1    Jun. 7, 2018

(30) Foreign Application Priority Data

Dec. 1, 2016    (IN) .............................. 201611041059

(51) Int. Cl.
| | |
|---|---|
| *H03K 3/00* | (2006.01) |
| *H04R 3/08* | (2006.01) |
| *B06B 1/02* | (2006.01) |
| *H03K 3/80* | (2006.01) |
| *G01S 13/82* | (2006.01) |
| *H03K 3/57* | (2006.01) |
| *H03K 17/567* | (2006.01) |

(Continued)

(52) U.S. Cl.
CPC ............. *H04R 3/08* (2013.01); *B06B 1/0215* (2013.01); *B06B 1/0269* (2013.01); *B06B 1/045* (2013.01); *G01N 29/041* (2013.01); *G01N 29/2412* (2013.01); *G01N 29/4436* (2013.01); *G01S 7/524* (2013.01); *G01S 13/82* (2013.01); *H03K 3/57* (2013.01); *H03K 3/64* (2013.01); *H03K 3/72* (2013.01); *H03K 3/78* (2013.01); *H03K 3/80* (2013.01); *H03K 17/567* (2013.01); *B06B 2201/54* (2013.01); *G01S 2007/4069* (2013.01)

(58) Field of Classification Search
CPC .. H04R 3/08; G01N 29/4436; G01N 29/2412; G01N 29/041; H03K 3/78; H03K 3/80; H03K 3/72; H03K 3/64; H03K 17/567; H03K 3/57; B06B 1/0215; B06B 2201/54; B06B 1/045; B06B 1/0269; G01S 7/524; G01S 13/82; G01S 2007/4069
USPC ......................................................... 327/110
See application file for complete search history.

(56) References Cited

U.S. PATENT DOCUMENTS

| | | | | |
|---|---|---|---|---|
| 3,760,388 A | * | 9/1973 | Schmitz .............. | G11B 20/1411 360/40 |
| 4,140,972 A | * | 2/1979 | Fletcher .............. | H04B 17/345 375/357 |

(Continued)

*Primary Examiner* — Ryan Jager
(74) *Attorney, Agent, or Firm* — Belles Katz LLC

(57) ABSTRACT

The present invention relates to an electromagnetic acoustic transducer excitation system comprising a tone burst generator, the tone burst generator comprising: an oscillator device configured to produce a radio frequency signal; an analog switch configured to produce an output based on the radio frequency signal produced by the oscillator device and a control signal; a pre-amplifier configured to amplify the output of the analog switch and produce a tone burst output signal; and a control module configured to produce the control signal for providing to the analog switch.

16 Claims, 3 Drawing Sheets

(51) Int. Cl.
    *G01N 29/04*     (2006.01)
    *B06B 1/04*     (2006.01)
    *G01S 7/524*     (2006.01)
    *H03K 3/64*     (2006.01)
    *H03K 3/72*     (2006.01)
    *H03K 3/78*     (2006.01)
    *G01N 29/24*     (2006.01)
    *G01N 29/44*     (2006.01)
    *G01S 7/40*     (2006.01)

(56) References Cited

U.S. PATENT DOCUMENTS

| | | | | |
|---|---|---|---|---|
| 4,575,720 A | * | 3/1986 | Smith | G08B 26/006 340/10.41 |
| 5,214,955 A | * | 6/1993 | Yost | G01N 29/075 374/119 |
| 5,426,388 A | | 6/1995 | Flora et al. | |
| 5,449,958 A | | 9/1995 | MacLauchlan et al. | |
| 6,250,163 B1 | | 6/2001 | MacLauchlan et al. | |
| 2003/0191409 A1 | * | 10/2003 | Yost | A61B 5/031 600/561 |
| 2009/0102443 A1 | | 4/2009 | Smith | |

* cited by examiner

ELECTROMAGNETIC ACOUSTIC TRANSDUCER EXCITATION SOURCE WITH PROGRAMMABLE TONE BURST GENERATOR

CROSS-REFERENCE TO RELATED APPLICATIONS

This application claims the benefit of Indian Patent Application No. 201611041059, filed Dec. 1, 2016. The disclosure of the above application is incorporated herein by reference.

DESCRIPTION

Field of the Invention

The present invention relates to an electromagnetic acoustic transducer excitation system comprising a tone burst generator. More particularly, the present invention relates to an improved design of the electromagnetic acoustic transducer excitation system comprising a tone burst generator with a provision of selectable number of cycles and burst repetition rate.

Background of the Invention

Non-contact generation of ultrasound using Electro-Magnetic Acoustic Transducer (EMAT) for non-destructive testing of electrically conducting materials is widely used. The approach has various advantages over conventional contact method which uses piezoelectric transducers. The excitation system of EMAT is unconventional and needs huge power of the order of 5 kW to 20 kW to be pumped into the coil for short duration. The coil is excited by a burst signal of specified frequency at certain repetition rate. Recently, it has been found from literature that the applications of EMAT has been increased due to its advantages but less data has been observed in the development of EMAT driving and related systems.

Reference may be made to Flora et al (U.S. Pat. No. 5,426,388) wherein disclosed a push-pull kind of EMAT power amplifier which utilizes high speed insulated gate bipolar transistor or metal oxide semiconductor controlled thyristor operatively connected to the main capacitor and the coil of transducer. The driving circuit is connected to this push-pull stage to feed square pulses to produce alternating current in the coil. An optical driving method is used to isolate the driver with power push-pull transistors. The invention is installed in the EMAT itself to avoid problems that occur due to long cable feeding Another reference is made to MacLauchlan et al (U.S. Pat. No. 5,449,958) wherein the disclosed invention is the diode expander for electromagnetic acoustic transducer. The invention is a transmit and receive (T/R) switch used to couple EMAT coil and a highly sensitive receiver. The circuit blocks the noise generated by the transmitter to enter into a sensitive receiver generally used with EMAT. A diode expander comprises pairs of diodes connected "back to back" that means with anode of one diode is connected to cathode of other. The arrangement allows high voltages and current to pass from the transmitter to the coil. The series connection of diodes effectively increases the blocking voltage. The circuit has limitation that the noise is propagated through diodes even without crossing the turn on voltage due to junction capacitance of the diodes.

Yet another reference is made to Stephen Smith (U.S. Patent 2009/0102443 A1). Herein the disclosed invention is about a new kind of circuit called H bridge to drive electromagnetic acoustic transducer (EMAT) which does not employ push-pull technology using a transformer but utilizes a new series MOSFET switches to correct the disadvantages associated with transformer circuit. The circuit has various advantages over conventional transformer method such as loss due to transformer and limitation of high frequency. It also describes paralleling method of H bridge and drive it in sequence.

Yet another reference is made to Daniel T. MacLauchlan (U.S. Pat. No. 6,250,163 B1). Herein the disclosed invention is an EMAT apparatus to test the weld spots non-destructively. The system uses two separate EMATs on two sheets welded. One EMAT works as transmitter whereas another EMAT work as receiver and kept on the other sheet. Personal computer is used to acquire signal and at least one parameter to relate to weld. In a pulse echo mode of weld testing the transducer is kept over the weld to be inspected and the echo pattern received is observed and analyzed. If the two plates are not weld the echoes received will have shorter spacing that perfect welded plates.

Therefore, it has been concluded that there is need of developing EMAT amplifier which neither work on the principle of push-pull nor H bridge. The excitation source also contains novel circuit of programmable tone burst generator with an option to select number of cycles in burst with repetition rate. The capability of having number of cycles selection gives advantage to test thin samples with relatively less mixing of the received echoes due to low time of flight associated with thin samples. Also, more number of cycles allows testing of thick and relatively higher attenuating materials. Low powers MOSFET are used in parallel to pump considerably high power in the EMAT coil. Paralleling of low power low cost MOSFETs significantly reduces the cost of output stage without compromising with the output power.

Objectives of the Invention

The main objective of the present invention is to provide a simple and low cost electromagnetic acoustic transducer (EMAT) excitation system comprising a tone burst generator which uses low power MOSFETs in parallel to pump high power to windings.

Another objective of the present invention is to provide new circuit design to generate tone burst needed to drive the EMAT power amplifier stage.

Yet another objective of the present invention is to provide tone burst design with capability to provide selection for number of cycles.

Yet another objective of the present invention is to provide the unique circuit with provision of selection of burst repetition rate.

Yet another objective of the present invention is to provide EMAT amplifier with built in completely isolated tone burst generator and no common ground.

SUMMARY OF THE INVENTION

Accordingly, the present invention provides electromagnetic acoustic transducer (EMAT) excitation system comprising a tone burst generator with an option to select number of cycles in a burst with repetition rate. An oscillating device has been used to generate 3.2 MHz continuous outputs. Alternatively, the oscillating device can be a suitable variable frequency source to generate tone burst of variable frequency. A comparator is used to compare the counts in a counter with reference pulses provided by a reference pulse source. The EMAT further comprises a power amplifier module configured to receive the tone burst output signal. The power amplifier module and tone burst generator are electrically isolated and thus have separate grounds.

These aspects and advantages will be more clearly understood from the following detailed description taken in conjunction with the accompanying drawings and claims.

BRIEF DESCRIPTION OF THE DRAWINGS

To further clarify advantages and aspects of the invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings, which are listed below for quick reference.

Figure 1:
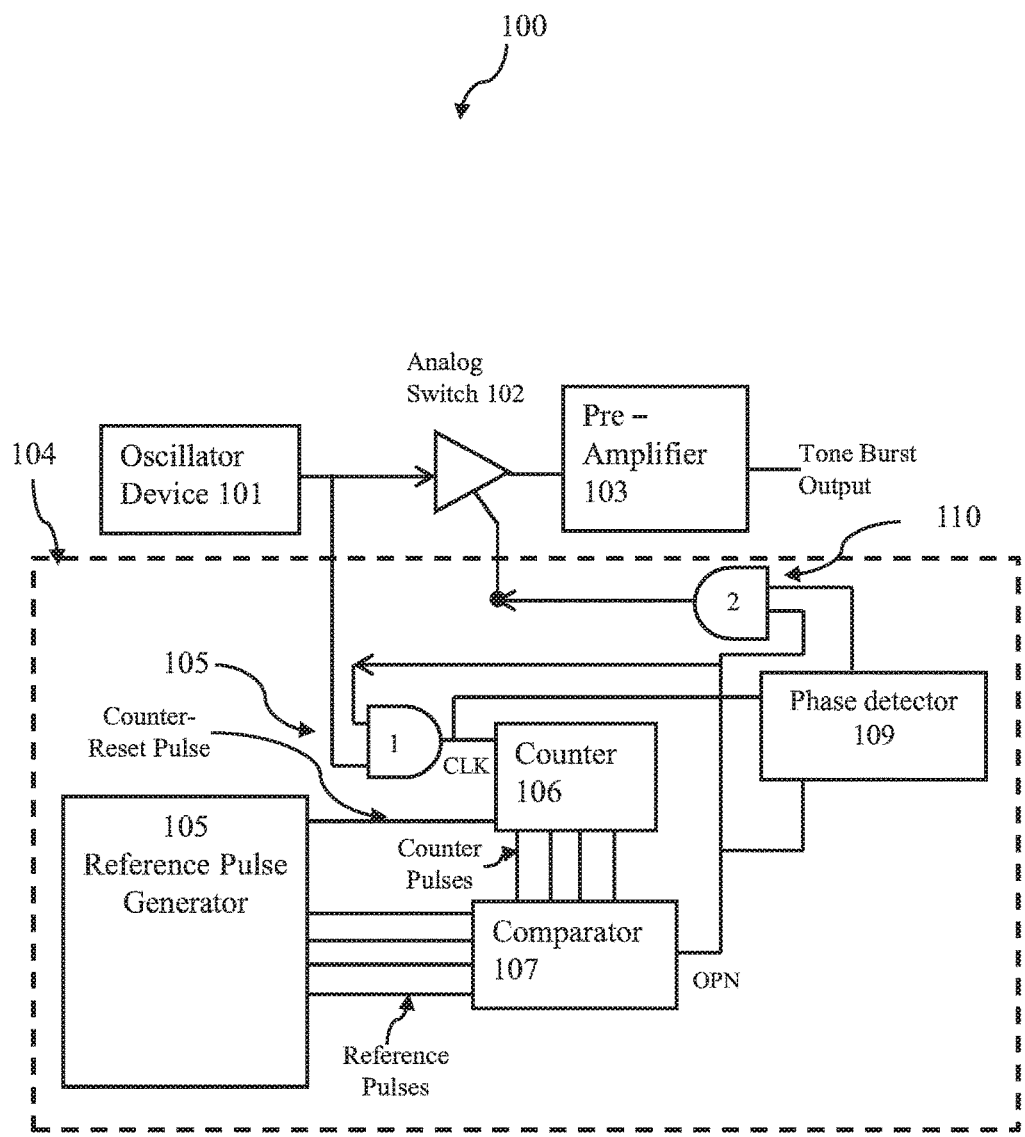
FIG. 1 schematically illustrates a tone burst generator of an electromagnetic acoustic transducer (EMAT) excitation system, in accordance with an embodiment of the present invention.

It may be noted that to the extent possible, like reference numerals have been used to represent like elements in the drawings. Further, those of ordinary skill in the art will appreciate that elements in the drawings are illustrated for simplicity and may not have been necessarily drawn to scale. For example, the dimensions of some of the elements in the drawings may be exaggerated relative to other elements to help to improve understanding of aspects of the invention. Furthermore, the one or more elements may have been represented in the drawings by conventional symbols, and the drawings may show only those specific details that are pertinent to understanding the embodiments of the invention so as not to obscure the drawings with details that will be readily apparent to those of ordinary skill in the art having benefit of the description herein.

DETAILED DESCRIPTION OF THE INVENTION

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof. Throughout the patent specification, a convention employed is that in the appended drawings, like numerals denote like components.

Reference throughout this specification to "an embodiment", "another embodiment" or similar language means that a particular feature, structure, or characteristic described in connection with the embodiment is included in at least one embodiment of the invention. Thus, the appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems.

Various embodiments of the invention will be described below in detail with reference to the accompanying drawings. Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

In accordance with the invention, an electromagnetic acoustic transducer (EMAT) excitation system comprises of unique tone burst generator with an option to select number of cycles in a burst with repetition rate. An oscillating device is used to generate radio frequency (RF) signal. A comparator is used to compare the counts in counter with a reference provided by reference pulse source. To start the burst output, a counter-reset pulse is sent to the counter by the reference pulse source. As the counter becomes zero, output of the comparator becomes high (active) and thus enables an AND gate to pass pulses to counter. Along with AND gate, output of the comparator also enables an analog switch to pass RF signal. However, the problem with the developed circuit is the non-synchronization of the counter-reset pulse and the start phase of RF signal. This results in the jitter on the tone burst output. In order to overcome this problem, an additional circuit has also been added by which waveform generation (zero phase angle) started at the time of counter-reset pulse. When output of comparator is high, the additional circuit enables the analog switch. When output of comparator is low, the additional circuit disables the analog switch.

Accordingly, FIG. 1 schematically illustrates a tone burst generator 100 of an electromagnetic acoustic transducer (EMAT) excitation system, in accordance with an embodiment of the present invention. The tone burst generator 100 includes an oscillator device 101 configured to produce a radio frequency signal; an analog switch 102 configured to produce an output based on the radio frequency signal produced by the oscillator device 101 and a control signal; a pre-amplifier 103 configured to amplify the output of the analog switch 102 and produce a tone burst output signal; and a control module 104 configured to produce the control signal for providing to the analog switch 102. The control module 104 comprises a reference pulse source 105; a counter 106, a comparator 107, a first AND gate (represented by numeral 1 for ease of reference) 108, a phase detector 109, and a second AND gate (represented by numeral 2 for ease of reference) 110. The phase detector 109 and the second AND gate 110 form the additional circuit to jitter on the tone burst output by synchronizing the counter-reset pulse and the start phase of RF signal.

Accordingly, the reference pulse source 105 is configured to produce reference pulses and counter-reset pulse. The counter 106 is configured to store counter pulses. The counter pulses are based on the radio frequency signal produced by the oscillator device 101. The counter 106 is furthermore configured to reset a count of the counter pulses based on the counter-reset pulse. The counter 106 being further configured to receive a counter clock input signal (represented in the figure as CLK).

The comparator 107 is configured to compare the reference pulses with counter pulses and produce an output signal indicative of a number of counter pulses being less than a number of reference pulses (represented in the figure as OPN for ease of reference).

The first AND gate 108 configured to receive a first input and a second input. The first input is being based on the radio frequency signal produced by the oscillator device 101 and the second input is being based the output from the comparator 107 indicative of a number of counter pulses being less than a number of reference pulses. The first AND gate 108 is further configured to produce the counter clock input signal for providing to the counter 106.

The phase detector 109 is configured to receive a first input and a second input. The first input is being based on the counter clock input signal of the first AND gate 108 and the second input is being based on the output from the comparator 107 indicative of a number of counter pulses being less than a number of reference pulses. The phase detector 109 is further configured to generate a phase detector output.

The second AND gate 110 is configured to receive a first input and a second input. The first input is being based on the phase detector output and the second input being based the output from the comparator 107 indicative of a number of counter pulses being less than a number of reference pulses. The second AND gate 110 is further configured to produce the control signal for providing to the analog switch 102.

In an implementation, the oscillator device 101 is a NOT gate based crystal oscillator. In an example, the oscillator device 101 is a fixed oscillator generating 3.2 MHz continuous RF signal. In another example, the oscillator device 101 is a suitable variable frequency source to generate tone burst of different frequency.

In an implementation, the counter 106 is at least a three-bit counter. In another implementation, the counter 106 is a four-bit counter.

In an implementation, the comparator 107 is at least a three-bit comparator. In another implementation, the comparator 107 is a four-bit comparator.

In an implementation, the reference pulse source 105 is a micro-controller. In another implementation, the reference pulse source 105 is a computing device. In another implementation, the reference pulse source 105 is a combination of thumbwheel switch with pulse repetition rate (PRR) generator.

In an implementation, the phase detector 109 is a monostable multi-vibrator.

In an implementation, the pre-amplifier 103 is of a cascaded common emitter type amplifier.

Further, the analog switch 103 comprises a first switch and a second switch controlled using a NOT gate. The first switch is configured to receive the radio frequency signal produced by the oscillator device 101 and a control input based on the control signal from the second AND gate 110. The first switch is being configured to pass the radio frequency signal as output when control signal from the second AND gate 110 is in a high state. The NOT gate is configured to receive the control signal from the second AND gate 110. The second switch defines an input terminal and a control terminal, the input terminal being electrically grounded, the control terminal being electrically connected to an output terminal of the NOT gate.

In operation, the tone burst output signal is started in response to receiving the counter-reset pulse from the reference pulse source 105. In response to the comparator 107 producing the output signal indicative of a number of counter pulses being less than a number of reference pulses, the first AND gate 108 is configured to pass the counter clock input signal to the counter 106; the phase detector 109 is configured to detect a raising edge of the counter clock input signal and generate the phase detector output; and the second AND gate 110 is configured to produce the control signal for providing to the analog switch 103 in response to receiving the phase detector output and the output signal indicative of a number of counter pulses being less than a number of reference pulses from the comparator 107.

Figure 2:
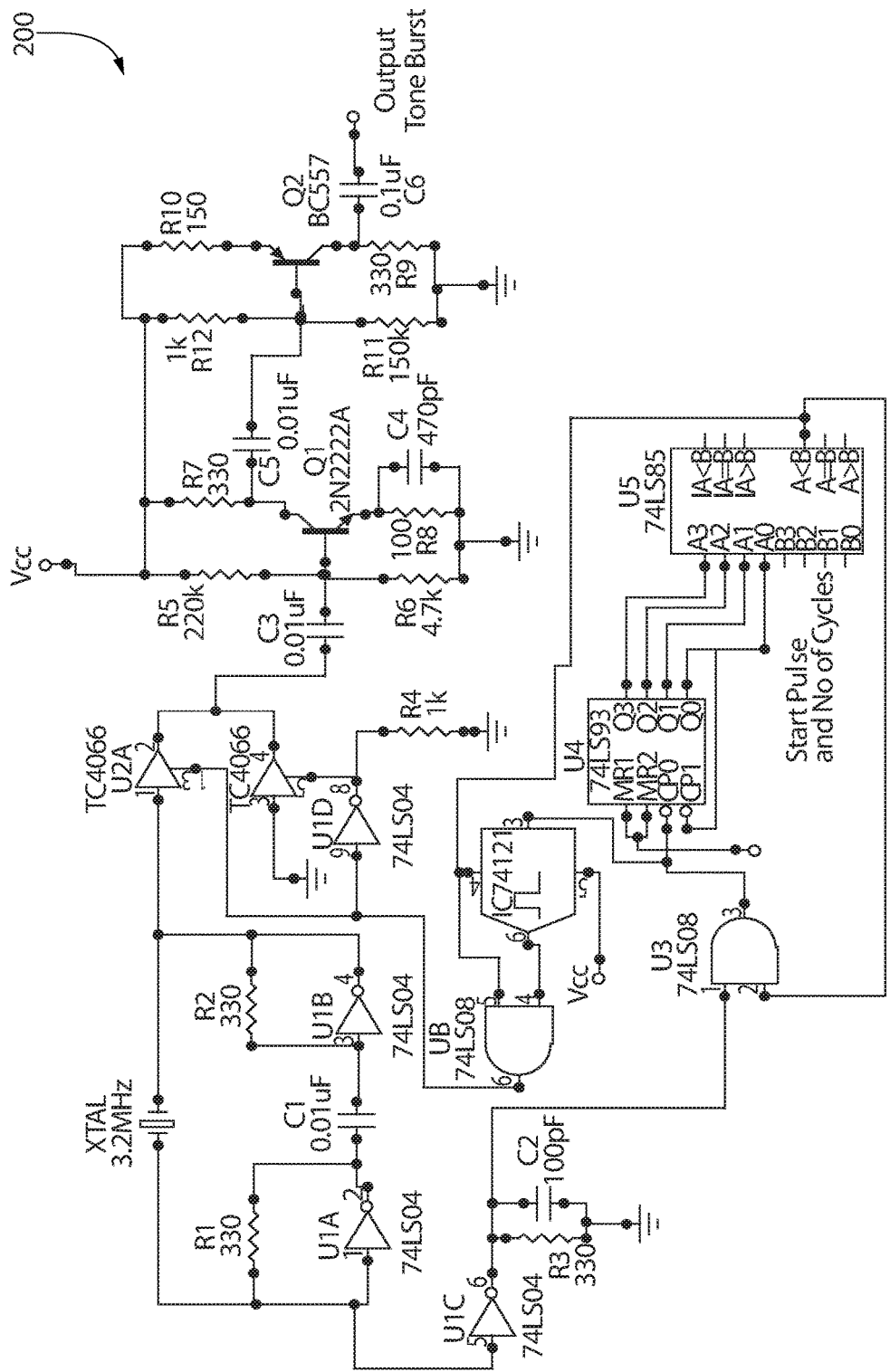
FIG. 2 illustrates a circuit implementation of the tone burst generator as described in FIG. 1, in accordance with embodiment of the present invention.

Accordingly, FIG. 2 illustrates a circuit implementation of the tone burst generator as described in FIG. 1.

Figure 3:
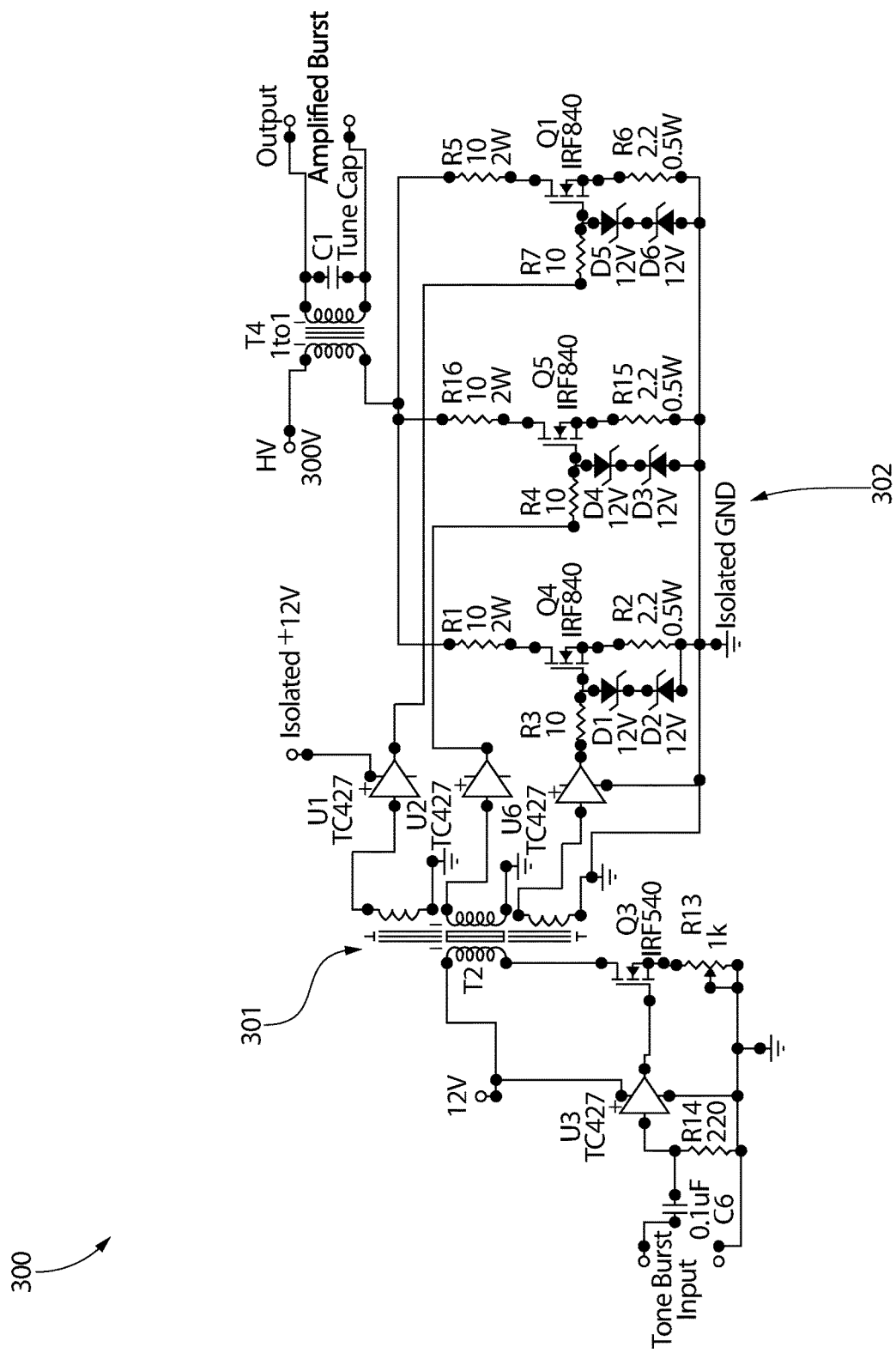
FIG. 3 illustrates a circuit implementation of power amplifier module in the EMAT, in accordance with the embodiment of the present invention.

FIG. 3 illustrates a circuit implementation of power amplifier module 300 in the EMAT, in accordance with the embodiment of the present invention. The power amplifier module 300 is configured to receive the tone burst output signal from the pre-amplifier 103 and produce an amplified tone burst output signal. The power amplifier module 300 is electrically isolated from the tone burst generator 100. In an implementation, the power amplifier module 400 comprises a RF transformer 301 comprising a primary winding and a series of secondary windings, and a series of MOSFET 302 based amplifiers connected to the outputs of each of the secondary winding. The power amplifier module 300 is designed using low MOSFETs in parallel to pump required amount of power in the windings.

EXAMPLES

The following examples are given by way of illustration of the working of the invention in actual practice by referring to the circuit implementations illustrated in the FIG. 3 and FIG. 4; and should not be construed to limit the scope of the present invention in any way.

Example 1

For the generation of radio frequency (RF) needed to excite the EMAT a NOT gates based crystal oscillator widely used has been preferred and used. Crystal was preferred to have stable frequency of 3.2 MHz. Here 3.2 MHz is selected based on the EMAT frequency however any suitable frequency may be used depending upon EMAT. For RF oscillator type any can be used having fixed or variable frequency option with amplitude of 2-3 Vpp.

Example 2

The analog switch used is CD 4066 or 4016 or any equivalent may be used to enable the RF oscillator to pass the selected no of cycles. While selecting the equivalent the on resistance and switching time of the switch must be as low as possible.

Example 3

4 bit counter and comparator are TTL 74LS93 and 74LS85 with AND gate 74LS08. However, any equivalent ICs (TTL or CMOS) can be used with their respective equivalents.

Example 4

IC 74LS121 has been utilized for the detection of rising edge of RF oscillator so that the analog switch will always be enabled at the same location of positive phase of cycle and avoids jitter in the burst. Any other edge sensitive chip may be used provided the gate must be enabling for sufficiently larger time to pass all specified number of cycles. In the present example 5 µs is selected for 3.2 MHz to pass 14 cycles easily though AND gate.

Example 5

The reference specifying number of cycles in a burst and start pulse to clear the counter is supplied by ATMEGA8535 microcontroller. However any microcontroller or computer may be used to send these signals. The reference signals may also be fed by a thumbwheel switch and a separate repetition rate oscillator which would essentially a square wave generator. The reference/start pulse may also be used from external device to synchronize.

Example 6

The RF transformer used to drive the power MOSFETs has a toroid core of 10-12 mm diameter with 3 turns in the primary and same number of individual turns in the secondary for isolated driving of the power transistors. The number of secondary windings indicates the number of MOSFETs to be paralleled.

Example 7

The parallel MOSFETs used are IRF840 to operate at 300V supply. Series resistances are added at the drain of each transistor to limit the pulsed current rating and avoid damage. Any equivalent or higher rated MOSFETs may be used with fast rise and fall times. The transformer used is a step down transformer to couple the burst output to EMAT coil. Suitable tuning capacitor is used to tune the output with EMAT coil.

Advantages

The main advantages of the present invention are:
1. The provision of providing specified number of cycles from 1 to 14 in the tone burst.
2. Provision to provide specified number of cycles from 1 to 10 in the tone burst without involving microcontroller. For instance, with a thumbwheel switch.
3. It provides capability to investigate thin samples with comparatively less mixing of echoes in pulse echo mode.
4. Provides capability to investigate thick/attenuating samples by transmitting more cycles per burst.
5. Paralleling of commonly available low cost MOSFETs reduce the overall cost.
6. Completely isolated with separate grounds of tone burst generator and power stage to protect any damage of burst generator stage due fault in high voltage power components.

While certain present preferred embodiments of the invention have been illustrated and described herein, it is to be understood that the invention is not limited thereto. Clearly, the invention may be otherwise variously embodied, and practiced within the scope of the following claims.

The invention claimed is:

1. An electromagnetic acoustic transducer excitation system comprising a tone burst generator, the tone burst generator comprising:
   an oscillator device configured to produce a radio frequency signal;
   an analog switch configured to produce an output based on the radio frequency signal produced by the oscillator device and a control signal;
   a pre-amplifier configured to amplify the output of the analog switch and produce a tone burst output signal; and
   a control module configured to produce the control signal for providing to the analog switch, the control module comprising:
   a reference pulse source configured to produce reference pulses and counter-reset pulse;
   a counter configured to store counter pulses, the counter pulses being based on the radio frequency signal produced by the oscillator, the counter being furthermore configured to reset a count of the counter pulses based on the counter-reset pulse, the counter being further configured to receive a counter clock input signal;
   a comparator configured to compare the reference pulses with counter pulses and produce an output signal indicative of a number of counter pulses being less than a number of reference pulses;
   a first AND gate configured to receive a first input and a second input, the first input being based on the radio frequency signal produced by the oscillator device and the second input being based the output from the comparator indicative of a number of counter pulses being less than a number of reference pulses, the first AND gate being configured to produce the counter clock input signal for providing to the counter;
   a phase detector configured to receive a first input and a second input, the first input being based on the counter clock input signal of the first AND gate and the second input being based on the output from the comparator indicative of a number of counter pulses being less than a number of reference pulses, the phase detector being further configured to generate a phase detector output; and
   a second AND gate configured to receive a first input and a second input, the first input being based on the phase detector output and the second input being based the output from the comparator indicative of a number of counter pulses being less than a number of reference pulses, the second AND gate configured to produce the control signal for providing to the analog switch.

2. The electromagnetic acoustic transducer excitation system as claimed in claim 1, further comprising: a power amplifier module configured to receive the tone burst output signal from the pre-amplifier and produce an amplified tone burst output signal.

3. The electromagnetic acoustic transducer excitation system as claimed in claim 2, wherein the power amplifier module is electrically isolated from the tone burst generator.

4. The electromagnetic acoustic transducer excitation system as claimed in claim 2, wherein the power amplifier module comprises a RF transformer comprising a primary winding, a series of secondary windings and a series of MOSFET based amplifiers connected to the outputs of each of the secondary winding.

5. The electromagnetic acoustic transducer excitation system as claimed in claim 1, wherein the oscillator device is a NOT gate based crystal oscillator.

6. The electromagnetic acoustic transducer excitation system as claimed in claim 1, wherein the counter is at least a three-bit counter.

7. The electromagnetic acoustic transducer excitation system as claimed in claim 1, wherein the counter is a four-bit counter.

8. The electromagnetic acoustic transducer excitation system as claimed in claim 1, wherein the comparator is at least a three-bit comparator.

9. The electromagnetic acoustic transducer excitation system as claimed in claim 1, wherein the comparator is a four-bit comparator.

10. The electromagnetic acoustic transducer excitation system as claimed in claim 1, wherein the reference pulse source is a micro-controller or a computing device or a combination of thumbwheel switch with pulse repetition rate (PRR) generator.

11. The electromagnetic acoustic transducer excitation system as claimed in claim 1, wherein the phase detector is a mono-stable multi-vibrator.

12. The electromagnetic acoustic transducer excitation system as claimed in claim 1, wherein the pre-amplifier is of a cascaded common emitter type amplifier.

13. The electromagnetic acoustic transducer excitation system as claimed in claim 1, wherein the analog switch comprises a first switch and a second switch controlled using a NOT gate.

14. The electromagnetic acoustic transducer excitation system as claimed in claim 13, wherein:
 the first switch is configured to receive the radio frequency signal produced by the oscillator device and a control input based on the control signal from the second AND gate, the first switch being configured to pass the radio frequency signal as output when control signal from the second AND gate is in a high state;
 the NOT gate is configured to receive the control signal from the second AND gate; and
 the second switch defines an input terminal and a control terminal, the input terminal being electrically grounded, the control terminal being electrically connected to an output terminal of the NOT gate.

15. The electromagnetic acoustic transducer excitation system as claimed in claim 1, wherein the tone burst output signal is started in response to receiving the counter-reset pulse from the reference pulse source.

16. The electromagnetic acoustic transducer excitation system as claimed in claim 1, wherein:
 in response to the comparator producing the output signal indicative of a number of counter pulses being less than a number of reference pulses, the first AND gate is configured to pass the counter clock input signal to the counter;
 the phase detector configured to detect a raising edge of the counter clock input signal and generate the phase detector output; and
 the second AND gate is configured to produce the control signal for providing to the analog switch in response to receiving the phase detector output and the output signal indicative of a number of counter pulses being less than a number of reference pulses from the comparator.

* * * * *